(12) United States Patent
Horrell

(10) Patent No.: US 6,905,022 B2
(45) Date of Patent: Jun. 14, 2005

(54) MEDICAL SUCTION DEVICE HOLDER

(76) Inventor: Scott Horrell, 2627 Leroy Dr., Cape Girardeau, MO (US) 63701

( * ) Notice: Subject to any disclaimer, the term of this patent is extended or adjusted under 35 U.S.C. 154(b) by 131 days.

(21) Appl. No.: 10/342,999

(22) Filed: Jan. 15, 2003

(65) Prior Publication Data

US 2003/0141209 A1 Jul. 31, 2003

Related U.S. Application Data

(60) Provisional application No. 60/349,855, filed on Jan. 17, 2002.

(51) Int. Cl.[7] .................................................. A47K 1/08
(52) U.S. Cl. ........................ 206/438; 206/363; 220/481; 248/311.2
(58) Field of Search ................................ 206/314, 363, 206/438; 220/476, 480, 481; 248/311.2

(56) References Cited

U.S. PATENT DOCUMENTS

| | | | | |
|---|---|---|---|---|
| 44,447 A | * | 9/1864 | O'Donnell ............... 248/285.1 |
| 832,754 A | * | 10/1906 | Smith ....................... 248/311.2 |
| 1,226,231 A | * | 5/1917 | Mack ..................... 211/119.009 |
| 1,797,077 A | * | 3/1931 | Dew et al. ................... 248/121 |
| D148,734 S | * | 2/1948 | Tackenberg et al. ......... D6/563 |
| 3,212,660 A | * | 10/1965 | Adell ......................... 248/313 |
| 5,580,020 A | * | 12/1996 | Catchings ................ 248/311.2 |
| 6,059,103 A | * | 5/2000 | Izen et al. ................... 206/314 |
| 6,260,811 B1 | * | 7/2001 | O'Neil ..................... 248/311.2 |

* cited by examiner

*Primary Examiner*—John A. Ricci
(74) *Attorney, Agent, or Firm*—Polster, Lieder, Woodruff & Lucchesi LP

(57) ABSTRACT

A holder for disposable medical suction tubes, common referred to as Yankauer suction tubes. The holder is adapted with a back panel for attachment to a vertical surface, an in particular, to an equipment column of the type commonly found in medical facilities such as an emergency treatment room. The holder is adapted to receive the sterile packaging of the Yankauer suction tube through a central bore in a supporting bracket affixed perpendicular to the back panel. A base plate secured perpendicular to the back panel below the supporting bracket provides a rest for the sterile packaging and suction tube.

12 Claims, 2 Drawing Sheets

MEDICAL SUCTION DEVICE HOLDER

CROSS-REFERENCE TO RELATED APPLICATIONS

The present application is based upon, and claims priority from, U.S. Provisional Patent application No. 60/349,855 filed on Jan. 17, 2002, and which is hereby incorporated by reference in entirety.

STATEMENT REGARDING FEDERALLY SPONSORED RESEARCH

Not Applicable.

BACKGROUND OF THE INVENTION

The present invention relates to devices for holding medical devices, and in particular, to a holder for disposable medical suction tubes and associated sterile packaging intended for use in hospital and medical facilities, such as intensive care units, critical care units, or cardio-thoracic units.

It is known in hospital facilities to utilize disposable holders for medical suction tube devices, and in particular, disposable holders which are designed as free-standing or clip-on attachment holders. These disposable holders are utilized one time, and may become contaminated with biohazard material during use, necessitating their disposal and replacement.

Accordingly, there is a need for a re-usable medical suction tube holder which may be secured to a stationary object, such as an equipment column, provide solid holding characteristics for medical suction tubes and associated sterile packaging between uses, and which is resistant to biohazard contamination, permitting subsequent cleaning and re-use.

BRIEF SUMMARY OF THE INVENTION

Briefly stated, the present invention provides a holder for disposable medical suction tubes, commonly referred to as Yankauer suction tubes. The holder is adapted for attachment to any vertical surface, and in particular, to an equipment column of the type commonly found in medical facilities such as an emergency treatment room. The configuration of the holder is adapted to receive the sterile packaging of the Yankauer suction tube, and to permit removal of the Yankauer suction tube from the sterile packaging without the need to remove the sterile packaging from the holder.

The foregoing and other objects, features, and advantages of the invention as well as presently preferred embodiments thereof will become more apparent from the reading of the following description in connection with the accompanying drawings.

BRIEF DESCRIPTION OF THE SEVERAL VIEWS OF THE DRAWINGS

In the accompanying drawings which form part of the specification.

Corresponding reference numerals indicate corresponding parts throughout the several figures of the drawings.

DESCRIPTION OF THE PREFERRED EMBODIMENT

Figure 1:
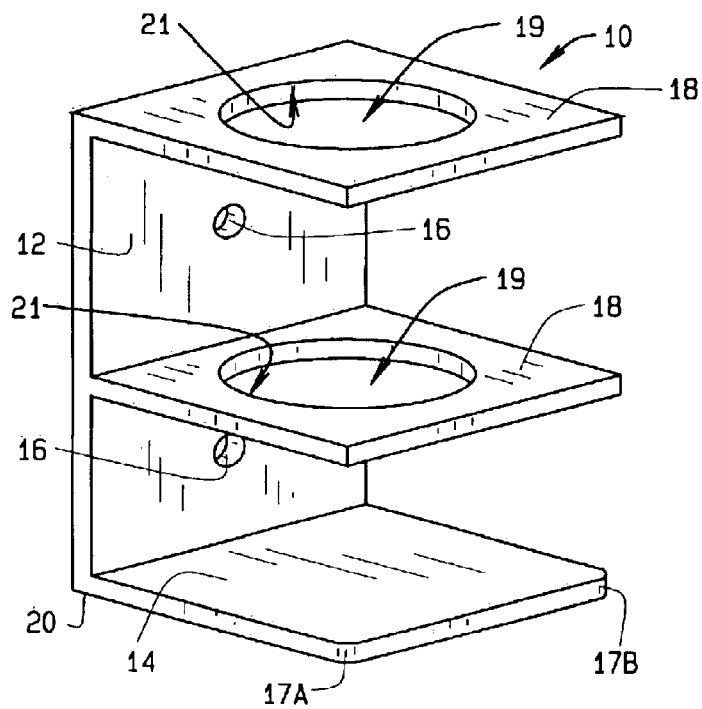
FIG. 1 is a perspective view of a first embodiment of the medical suction tube holder of the present invention.
Figure 3:
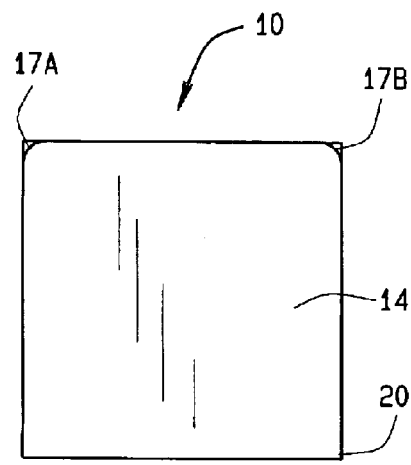
FIG. 3 is a bottom plan view of the medical suction tube holder of FIG. 1.
Figure 2:
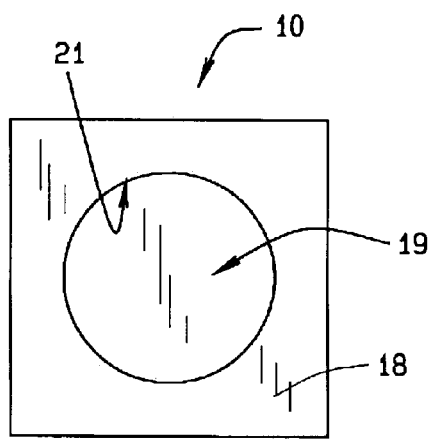
FIG. 2 is a top plan view of the medical suction tube holder of FIG. 1.
Figure 4:
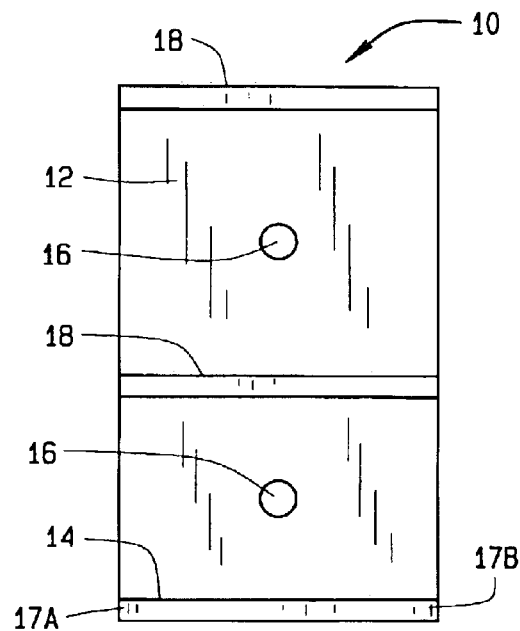
FIG. 4 is a front plan view of the medical suction tube holder of FIG. 1.
Figure 5:
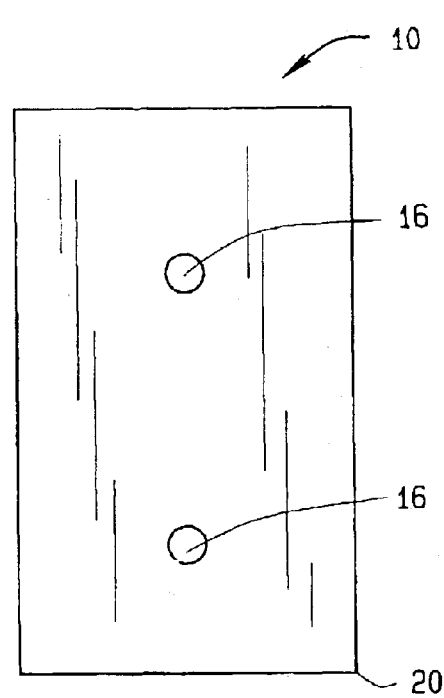
FIG. 5 is a rear plan view of the medical suction tube holder of FIG. 1.
Figure 6:
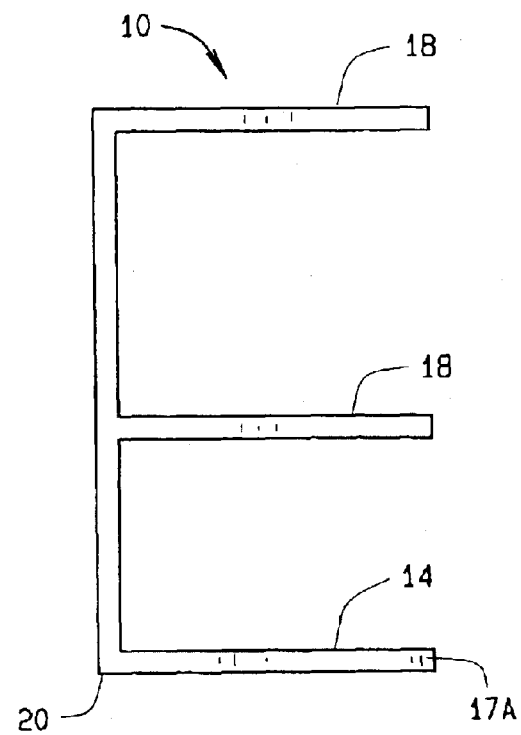
FIG. 6 is a left side plan view of the medical suction tube holder of FIG. 1.

The following detailed description illustrates the invention by way of example and not by way of limitation. The description clearly enables one skilled in the art to make and use the invention, describes several embodiments, adaptations, variations, alternatives, and uses of the invention, including what is presently believed to be the best mode of carrying out the invention.

Turning to FIG. 1 through FIG. 6, a medical suction tube holder of the present invention is illustrated generally at 10. The preferred embodiment of the medical suction tube holder 10 comprises a supporting back panel 12, a lower base platform 14, and one or more tube receiving and supporting brackets 18.

The supporting back panel 12 includes at least one mounting hole 16 through which a mounting screw or similar attachment component (not shown) can pass, permitting the supporting back panel 12 to be secured to a planar surface such as a wall or equipment column (not shown). Preferably, at least two mounting holes 16 are spaced apart on the supporting back panel 12, permitting the panel to be secured to a vertical surface with conventional fasteners in such a manner that it will not pivot or shift about the fasteners (not shown). Those skilled in the art will recognize that alternative mounting components may be utilized, including hooks, Velcro, or adhesive, (not shown) which do not require the use of one or more mounting holes 16 through the supporting back panel 12.

Figure 7:
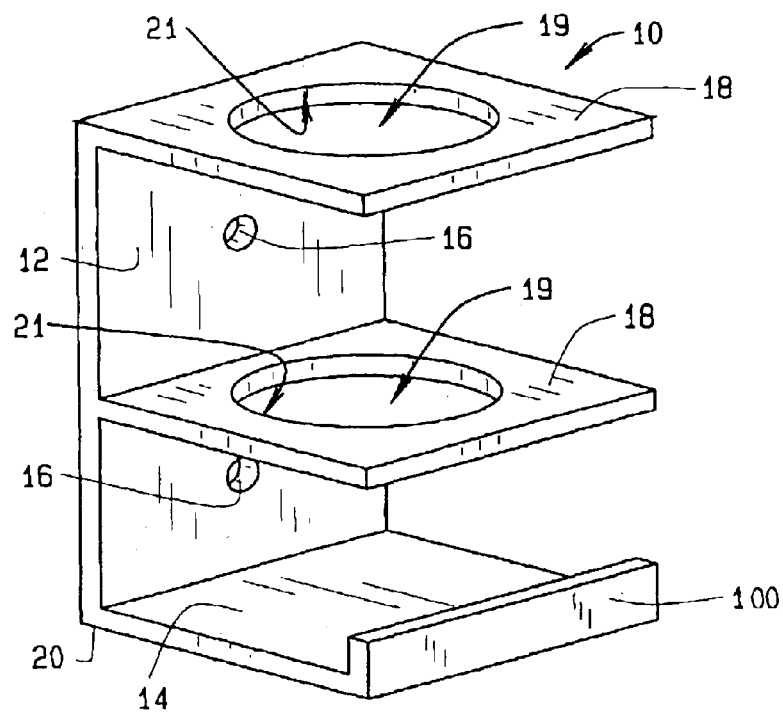
FIG. 7 is a perspective view of a second embodiment of the medical suction tube holder of the present invention.

The lower base platform 14 preferably is disposed perpendicular to the back panel 12, at the bottom edge 20 thereof, providing a horizontal resting surface when the back panel 12 is secured in a vertical orientation. The base platform 14 is preferably square in shape, having a width and depth equal to the width of the supporting back panel 12. The corners 17A and 17B of the base platform 14, disposed away from the attachment point to the supporting back pane 12, may be truncated or rounded to eliminate any right angles or sharp edges. Optionally, as shown in FIG. 7, in an alternate embodiment, the lower base platform 14 may include a raised lip 100 on one or more of peripheral edges.

Spaced apart from the lower base platform 14 are one or more supporting brackets 18 disposed perpendicularly to the back panel 12. Each supporting bracket 18 includes a central bore or circular pass-through opening 19, and preferably has the same dimensions as the lower base platform 14. The circular pass-through opening 19 is centrally disposed in the supporting bracket 18, such that a medical suction tube (not shown), including disposable sterile packaging (not shown), placed through the openings 19 will rest on the lower base platform 14, and be supported by the inner peripheral edges 21 of the openings 19 in the supporting brackets 18, shown in FIG. 1.

Preferably, the medical suction tube holder 10 of the present invention is formed from steel, and provided with a hygienic powder coat finish, including an anti-microbial surface coating. Those of ordinary skill in the art will recognize that a variety of suitable materials may be utilize to construct the suction tube holder 10, and that a number of different anti-microbial, anti-bacterial, or anti-fungal coatings may be employed to inhibit the growth or transmission of various infectious bacteria, such as staph bacteria, *e-coli*, and *salmonella*.

Those of ordinary skill in the art will further recognize that by forming the base platform 14 and at least one supporting bracket 18 with the same width and depth dimensions facilitates construction of the medical suction tube holder 10 of the present invention from a single contiguous piece of material. Additional supporting brackets 18 may be cut from the single contiguous piece of material and secured to the supporting back panel 12 in a conventional manner.

In view of the above, it will be seen that the several objects of the invention are achieved and other advantageous results are obtained. As various changes could be made in the above constructions without departing from the scope of the invention, it is intended that all matter contained in the above description or shown in the accompanying drawings shall be interpreted as illustrative and not in a limiting sense.

What is claimed is:

1. A medical device holder comprising:
   a supporting planar back panel defining a front surface and a rear surface;
   a base plate perpendicularly affixed to said front surface of said planar back panel adjacent a lower edge;
   at least one planar supporting bracket perpendicularly affixed to said front surface of said planar back panel apart from said base plate, said planar supporting bracket including a central bore disposed vertically above said base plate; and
   wherein said supporting planar back panel and said at least one planar supporting bracket have a common width; and
   wherein said base plate further includes at least one raised peripheral lip.

2. The medical device holder of claim 1 further including an anti-microbial characteristic.

3. The medical device holder of claim 1 wherein said supporting planar back panel is configured for attachment to a vertical surface.

4. The medical device holder of claim 1 wherein said supporting planar back panel further includes at least one mounting hole extending from said front surface to said rear surface, said at least one mounting hole configured to receive a mounting means for securing said medical device holder to said vertical surface.

5. The medical device holder of claim 4 wherein said supporting back panel is configured with a mounting means disposed on said rear surface for attachment to said vertical surface.

6. The medical device holder of claim 1 wherein at least said base plate and said at least one planar supporting bracket are integrally formed with said supporting planar back panel.

7. A medical device holder comprising:
   a supporting planar back panel defining a front surface and a rear surface;
   a base plate perpendicularly affixed to said front surface of said planar back panel adjacent a lower edge;
   a first planar supporting bracket perpendicularly affixed to said front surface of said planar back panel apart from said base plate, said first planar supporting bracket including a central bore disposed vertically above said base plate; and
   a second planar supporting bracket perpendicularly affixed to said front surface of said planar back panel, said second planar supporting bracket including a second central bore axially aligned with said central bore of said first planar supporting bracket, said central bore and said second central bore each having a common radial dimension, said second planar supporting bracket disposed between said first planar supporting bracket and said base plate; and
   wherein said supporting planar back panel, said first planar supporting bracket, and said second planar supporting bracket have a common width.

8. The medical device holder of claim 7 further including an anti-microbial characteristic.

9. The medical device holder of claim 7 wherein said supporting planar back panel is configured for attachment to a vertical surface.

10. The medical device holder of claim 7 wherein said supporting planar back panel further includes at least one mounting hole extending from said front surface to said rear surface, said at least one mounting hole configured to receive a mounting means for securing said medical device holder to said vertical surface.

11. The medical device holder of claim 10 wherein said supporting back panel is configured with a mounting means disposed on said rear surface for attachment to said vertical surface.

12. The medical device holder of claim 7 wherein at least said base plate and said first planar supporting bracket are integrally formed with said supporting planar back panel.

* * * * *